United States Patent [19]

Mehta et al.

[11] Patent Number: 5,171,467
[45] Date of Patent: Dec. 15, 1992

[54] SYNTHESIS OF ORGANOMETALLIC/ORGANOBIMETALLIC COMPOSITIONS

[75] Inventors: Vijay C. Mehta; Robert C. Morrison; Conrad W. Kamienski, all of Gastonia, N.C.

[73] Assignee: FMC Corporation, Philadelphia, Pa.

[21] Appl. No.: 488,901

[22] Filed: Mar. 6, 1990

[51] Int. Cl.$^5$ .............................. C09K 3/00; C07F 3/02
[52] U.S. Cl. ................................. 252/182.3; 260/665 R
[58] Field of Search ................... 252/182.3; 260/665 R

[56] References Cited

U.S. PATENT DOCUMENTS

| | | | |
|---|---|---|---|
| 3,155,736 | 11/1964 | Beumel | 260/665 R |
| 3,293,313 | 12/1966 | Borkowski | 260/665 R |
| 3,534,113 | 10/1970 | Eastham et al. | 260/665 R |
| 3,716,495 | 2/1973 | Hsieh | 502/153 |
| 3,822,219 | 7/1974 | Kamienski et al. | 502/153 |
| 3,886,089 | 5/1975 | Smith | 502/157 |
| 4,128,501 | 12/1978 | Smith et al. | 502/153 |
| 4,207,207 | 6/1980 | Sanchez et al. | 502/152 |
| 4,213,880 | 7/1980 | Knight et al. | 502/156 |
| 4,222,969 | 9/1980 | Fanin et al. | 502/152 |
| 4,249,029 | 2/1981 | Hennart et al. | 585/638 |
| 4,342,708 | 8/1982 | Sakurai et al. | 502/156 |
| 4,429,054 | 1/1984 | Morrison | 502/157 |
| 4,615,843 | 10/1986 | Fannin et al. | 260/665 R |
| 4,976,886 | 12/1990 | Morrison et al. | 252/182.3 |

OTHER PUBLICATIONS

Gilman and Gaj, Journal of Organic Chemistry, 1957, vol. 22, pp. 165–168.

H. O. Houseand M. Gall, Organic Synthesis, 1972, vol. 52, pp. 39–52.

*Primary Examiner*—Edward A. Miller
*Attorney, Agent, or Firm*—Charles C. Fellows; Conrad W. Kamienski

[57] ABSTRACT

A process for producing organometallic and/or organobimetallic compositions by reacting an organic halide, an alkali metal and magnesium halide in a liquid hydrocarbon solvent containing a limited amount of a Lewis base to produce a dialkyl magnesium compound or a dialkyl magnesium compound complexed with an alkali metal organic compound.

14 Claims, No Drawings

SYNTHESIS OF ORGANOMETALLIC/ORGANOBIMETALLIC COMPOSITIONS

This invention relates to producing organometallic-/organobimetallic compositions by reacting an organohalide with an alkali metal to form an organolithium compound which is concurrently or subsequently exchanged with anhydrous magnesium halide in a hydrocarbon solvent containing no more than two moles of a Lewis base per mole of organohalide to produce the desired organometallic or organobimetallic composition.

Alkyllithium compounds, particularly methyllithium (MeLi), are used as reagents in the preparation of pharmaceuticals and special chemicals. Methyllithium has been commercially available in diethyl ether solutions containing an equivalent of lithium bromide formed as a by-product and remaining in solution as a complex with methyllithium. While useful in organic syntheses, inorganic halide free solutions of methyllithium in diethyl ether are pyrophoric. Methyllithium solutions in pure THF are not thermally stable. Gilman and Gaj in Journal of Organic Chemistry, 22, 1164 (1957) disclose preparing methyllithium from methyl chloride and lithium metal in tetrahydrofuran (THF). The THF/Li mole ratio was 9.8 to 1 which indicates use of a large excess of THF. Even at 0° C. these products had poor thermal stability.

Copending U.S. patent application Ser. No. 160,388 filed Feb. 25, 1989 now U.S. Pat. No. 4,976,886 issued Dec. 11, 1990, discloses a process for producing organobimetallic compositions by reacting an organic halide with a mixture of lithium and magnesium metals in a hydrocarbon solvent in the presence of 0.5 to 2 moles of a Lewis base per mole of halide. The alkyllithium solutions produced by this process have improved thermal stability at temperatures up to at least 40° C. due to the presence of a stabilizing amount of a dialkylmagnesium compound. The process was quite useful in producing small quantities of stabilized alkyllithium compositions, such as methyllithium containing seven mole percent dimethylmagnesium, but when the process was scaled up to produce large amounts of product the amount of dimethylmagnesium produced was found to be erratic and in some cases about fifty percent lower than expected. A process that predictably produces bimetallic compositions with the desired amounts of each metal is needed to achieve the desired product thermal stability.

The present invention provides an improved process for producing organometallic or organobimetallic compositions comprising reacting an organo halide, in a liquid hydrocarbon solvent containing a limited amount of a Lewis base, with an alkali metal and anhydrous magnesium halide. The product formed is an alkali metal alkyl complexed with a dialkylmagnesium or the product will be only or primarily dialkylmagnesium and by product alkali metal halide. The reaction can be conducted stepwise; first the alkali metal is reacted with the alkyl halide to produce an alkali metal alkyl; then the alkali metal alkyl is reacted with anhydrous magnesium halide to form a dialkyl magnesium compound which in most instances is complexed with an alkali metal alkyl compound. The magnesium halide can be added prior to the alkali metal-organic halide reaction or added after the alkyl halide-alkali metal reaction.

When excess alkali metal and organic halide are employed the product additionally contains an alkali metal organic compound such as an alkali metal alkyl, for example methyllithium. The process is represented by the following chemical equation in which the alkyl halide group is methyl chloride:

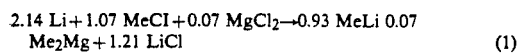

$$2.14\ Li + 1.07\ MeCl + 0.07\ MgCl_2 \rightarrow 0.93\ MeLi\ 0.07\ Me_2Mg + 1.21\ LiCl \quad (1)$$

The reactants in this process can be varied to produce innumerable products containing 0 to 98 mole percent of an alkali metal alkyl compound and 2 to 100 mole percent of a dialkylmagnesium compound. The reactant variation can best be shown by the following reactions [see chemical equations below] which occur sequentially to produce methyllithium (MeLi) compositions or dimethylmagnesium (Me$_2$Mg):

$$2Li + MeCl \rightarrow MeLi + LiCl \quad (2)$$

$$2MeLi + MgCl_2 \rightarrow Me_2Mg + LiCl \quad (3)$$

First MeLi is formed by the reaction between Li and methyl chloride (MeCl), illustrated in (equation 2), and then the MeLi reacts with the activated magnesium chloride (MgCl$_2$) to produce dimethylmagnesium (equation 3) containing 0 to 98 mole percent alkali metal compound as follows:

Assuming the lithium and magnesium chloride to be 100% active, the range of mole ratios of Li metal to MeCl to MgCl$_2$ is from 2 to 1 to 0.02–0.5.

Most preferably to produce a MeLi/Me$_2$Mg composition containing 93 mole percent MeLi and 0.07 mole percent dimethylmagnesium (see chemical equation 1) a mole ratio of Li to MeCl to MgCl$_2$ of 2 to 1 to 0.07 would be required.

To produce dimethylmagnesium containing no methyllithium (see chemical equation 5) one employs a mole ratio of Li to MeCl to MgCl$_2$ of 2 to 1 to 0.5.

A further example to show reagent variations, which produce a MeLi/Me$_2$Mg composition (50/50 mole%), requires a Li to MeCl to MgCl$_2$ of 2 to 1 to 0.333 (see equation 4) Thus, by varying the MgCl$_2$, and while a 2/1 mole ratio of Li/MeCl is held constant, dimethylmagnesium and innumerable MeLi/Me$_2$Mg compositions can be synthesized.

The process of the invention when producing alkali metal alkyls reacts an alkali metal, selected from sodium, potassium or lithium, preferably lithium metal, most preferably lithium containing some sodium metal with an alkyl halide and an anhydrous magnesium chloride in a hydrocarbon solvent containing a small amount of a Lewis base such as THF. The alkali metal is preferably finely divided and dispersed or slurried in an aromatic hydrocarbon containing tetrahydrofuran. The alkyl halide, preferably methyl or ethyl halide is added to the slurried lithium metal while the temperature is maintained between 0° C. and about 50° C.; preferably the temperature is maintained between 25° C. and 35° C. It is preferred to activate or condition the finely divided alkali metal, such as lithium metal by stirring it together with a small amount of alkyllithium in the selected solvent for a short period before reaction with the alkyl halide. This appears to increase the reactivity of the lithium metal. Typically, the alkyl halide is added slowly to the alkali metal slurry with agitation as this facilitates control of the reaction temperature. The reactions involving an alkali metal are done under an inert atmosphere, preferably argon. The product is a tetrahydrofuran complex of an alkali metal alkyl, which contains a dialkylmagnesium compound or mixtures of dialkylmagnesium compounds, in a hydrocarbon solvent.

A method or process variable having a great influence on yield is the amount of Lewis base, such as tetrahydrofuran, present during the reaction. While the ratio of tetrahydrofuran to alkyl halide may vary between about 0.05 and about 2.0 moles of Lewis base per mole of methyl halide; in the case of tetrahydrofuran and methyl halide, the preferred range is about 1.2 to 1.5 moles of tetrahydrofuran per mole of methyl halide. Surprisingly, higher and lower levels of tetrahydrofuran (THF) tend to result in lower yields.

Organo halides useful in practicing this invention may be represented by the formula RX in which X is selected from the group consisting of chloride, bromide and iodide; and R is selected from the group of alkyl, cycloalkyl, α-alkylene, alkenyl and aryl groups. More specifically, R can be selected from the group consisting of methyl, ethyl, n-butyl, sec-butyl, 2-ethylhexyl, n-octyl, cyclohexyl, 1,4-butylene, phenyl, cumyl, benzyl, tolyl, vinyl and crotyl groups. When desired, mixtures of different organohalides can be employed to produce mixed organic groups in the products of this invention.

The anhydrous magnesium halide is selected from magnesium bromide, magnesium chloride or magnesium iodide or mixtures thereof. Magnesium chloride is preferred as being least expensive and least soluble in the final product.

The liquid hydrocarbon solvents used in practicing this invention are typically selected from aliphatic hydrocarbons containing five to ten carbon atoms, alicyclics containing six to ten carbon atoms and aromatic hydrocarbons such as benzene, toluene, ethylbenzene, cumene and so forth, and mixtures thereof. The solubility of methyllithium, even when stabilized with dimethylmagnesium, lithium bromide or lithium iodide is such that at least some of the solvent must be an aromatic solvent.

Unexpectedly, when anhydrous magnesium halide is present at the beginning of the lithium metal-methyl chloride reaction to prepare lower alkyl lithium compounds, such as methyllithium, little or no metallation of the aromatic solvent takes place. Metallation of the aromatic solvent is the principal degradation route for methyllithium solutions in an aromatic hydrocarbon containing a limited amount of Lewis base. This is an important advantage of the present process, especially when making methyllithium, since a preferred solvent is cumene and avoiding or minimizing formation of by-product cumyllithium is necessary as it is an impurity of concern to some end users of methyllithium.

Apparently when anhydrous magnesium halide is present at the beginning of the reaction between lithium metal and methyl chloride the reaction first occurs between lithium and methyl chloride and then the reaction proceeds between methyllithium and magnesium chloride to produce the desired dimethyl magnesium and by-product lithium chloride. This is surprising in view of the known competing reaction in which lithium metal reduces magnesium dichloride to magnesium metal and lithium chloride.

Another advantage of the present process over prior processes is that the amount of magnesium present as dimethylmagnesium ($Me_2Mg$) in a given preparation can be varied according to how much anhydrous magnesium chloride is employed example, synthesis of a $MeLi/Me_2Mg$ composition (50/50 mole %) is illustrated by the following chemical equation:

$$6 Li + 3 MeCl + MgCl_2 \rightarrow MeLi + Me_2Mg + 5 LiCl \quad (4)$$

Similarly it is possible to reduce the amount of lithium available for the reactions still further to synthesize dimethylmagnesium according to the following chemical equation:

$$4 Li + 2 MeCl + MgCl_2 \rightarrow Me_2Mg + 4 LiCl \quad (5)$$

The yields of methyllithium and dimethylmagnesium are uniformly high in this new process, greater than 90% as is obtained in the process of U.S. Ser. No. 160,388 noted above. This is somewhat surprising in view of the possible reduction of anhydrous magnesium chloride by lithium metal.

Yet another advantage of the present process is that magnesium chloride can be added at the end of the reaction to adjust the magnesium level upward if desired. The magnesium content, in a product having a low magnesium content, can be adjusted; for example, a product having a $MeLi/Me_2Mg$ ratio of 100/04 can be adjusted to give a ratio close to 93/07 according to the following chemical equation:

$$1.0\ MeLi + .04\ Me_2Mg + 0.035\ MgCl_2 \rightarrow 0.93\ MeLi + 0.075\ Me_2Mg + 0.07\ LiCl$$

A preferred anhydrous magnesium chloride for use in this invention is a by-product of the Kroll process for the production of titanium or zirconium. This process produces anhydrous magnesium chloride when transition metal halides are heated at about 900° C. in the presence of magnesium metal. Under helium or argon, titanium tetrachloride is metered into a stainless steel reaction vessel which contains molten magnesium. The highly exothermic reaction is controlled by the feed rate of titanium tetrachloride. Molten magnesium chloride is tapped from the bottom of the reactor. The solid magnesium chloride is then crushed and/or ground and packaged into drums. This magnesium chloride is very active and will exchange with alkyllithiums, such as methyllithium, in solution in hydrocarbons which contain a Lewis base (THF, etc.), such as methyllithium to produce a dialkylmagnesium. However, since magnesium chloride is very hydroscopic, its activity (ability to exchange) is dependent on how well it is protected from moisture during grinding, packaging, and storage. Thus, depending on these variables, the activity of the anhydrous magnesium chloride could vary from lot to lot; lab testing for water content and activity would be a prerequisite prior to plant use. Once water is picked up by magnesium chloride, such water is very difficult to remove by drying, and, in fact, during dehydration the $MgCl_2$ may be deactivated and then it will not undergo metal-metal exchange reactions efficiently.

The following Examples further illustrate the invention.

EXAMPLE I (EXPERIMENT 6595)

This experiment was conducted using a one liter glass reaction flask, dry ice condenser, gas inlet, thermometer, filter funnel, mechanical stirrer with associated equipment, and a cooling bath (solid carbon dioxide in hexane).

All glassware was baked in an oven (~150° C.) for several hours, assembled, and purged with argon until cool. An argon atmosphere was maintained throughout reaction, filtration, and packaging. Magnesium chloride (14.1 g), cumene (150 ml), and THF (89.5 g) were added to the reaction assembly. Then, MeLi (10 ml) was added slowly (dropwise) to the stirred slurry. Some trace amount of methane gas evolved due to the reaction of methyllithium with a small amount of water contained in the magnesium chloride. The mass was stirred for about 30 minutes; and then pre-washed lithium dispersion (18.2 g), cumene (335 ml), and methyllithium (10 ml) were added. Stirring was continued for an additional 30 minutes. The reaction was initiated with methyl chloride (1 g) as indicated by a 7° C. temperature rise (27° to 34° C.). The remaining methyl chloride (52.4 g) was added as a gas slowly over a time period of one hour and seven minutes while controlling the reaction temperature at 34° C. ±2° C. The reaction mass was stirred for two additional hours in order to ensure complete reaction of the methyl chloride. The filtration was rapid (15 min.) yielding 646 g of light yellow, clear MeLi/Me$_2$Mg solution. This experiment was repeated several times varying the reactant ratios which are reported in Table I.

| Analytical Results |
| --- |
| Total Base = 1.30 N |
| Mg Titration = 0.07 M |
| NMR = 1.27 N MeM |
| = 1.21 mole ratio THF/MeM |
| Soluble Inorganic = 1360 ppm |
| Chloride Titration |
| I.C.P. Analyses = 1.15 M Li |
| = 0.07 M Mg |
| Recovered Yield = 92.4% (based on MeCl used) |

| Analytical Results -continued |
| --- |
| Utilization MgCl$_2$ = 37.2% |
| Composition (MeLi/Me$_2$Mg) = 94.4/5.6 mole ratio |

EXAMPLE II (EXPERIMENT 6612)

A pyrex bottle (125 ml) containing a magnetic stirring bar was baked in an oven (150° C.) for six hours. The bottle was purged with argon until cool, and then magnesium chloride (1.11 g) was added to the bottle, which was then fitted with a rubber septum. MeLi/Me$_2$Mg (94/06 mole ratio) solution (50 ml) was then charged via a syringe. The contents of the bottle was stirred for five hours. Filtration resulted in a clear, light yellow MeLi/Me2Mg solution.

| Analytical Results |
| --- |
| Total Base = 1.26 N |
| Mg Titration = 0.29 M |
| NMR = 1.26 N MeM |
| = 1.31 mole ratio THF/MeM |
| Soluble Inorganic = 570 ppm |
| Chloride Titration |
| I.C.P. Analysis = 0.73 M Li |
| = 0.28 M Mg |
| Utilization MgCl$_2$ = 92.7% |
| Composition (MeLi/Me$_2$Mg) = 70.1/29.9 mole ratio |

This experiment demonstrates, using the process of the invention, that it is possible to increase the magnesium content of a methyllithium/dimethylmagnesium composition having starting mole ratios, respectively, of 94 to 6. The experiment was repeated a number of times to prepare new compositions having various methyllithium to dimethylmagnesium ratios. The various experiments, reactant ratios, analytical data, and new composition details are reported in Table II.

TABLE I

SYNTHESIS OF MeLi/Me$_2$Mg SOLUTIONS IN THE THF/CUMENE VIA LITHIUM, METHYLCHLORIDE, AND MAGNESIUM CHLORIDE

| | Materials | | | | | Analytical Results | | | | | | |
| --- | --- | --- | --- | --- | --- | --- | --- | --- | --- | --- | --- | --- |
| Exp. No. | Lithium Moles | MeCl Moles | MgCl$_2$ Moles | THF Moles | Cumene ml | Total Base N. | Mg Titration N. | Chloride (1) Titration ppm | NMR MeM N. | NMR THF/MeM Mole Ratio | Yield MeM % | Composition MeLi/Me$_2$Mg Mole Ratio | Utilization (2) MgCl$_2$ % |
| 6611 | 2.30 | 1.00 | 0.09 (3,5) | 1.24 | 485 | 0.65 | 0.10 | 1240 | N.A. | N.A. | 52.3 | 81.8/18.2 | 85.0 |
| 348-41 | 2.30 | 0.98 | 0.12 (3,6) | 1.18 | 485 | 1.45 | 0.15 | 1230 | 1.41 | 1.22 | 96.4 | 88.5/11.5 | 84.2 |
| 6592 | 2.90 | 1.02 | 0.09 (4,5) | 1.24 | 485 | 1.42 | 0.06 | 1500 | 1.38 | 1.24 | 91.0 | 95.4/4.6 | 45.6 |
| 6595 | 2.60 | 1.06 | 0.15 (4,5) | 1.24 | 485 | 1.30 | 0.07 | 1367 | 1.27 | 1.21 | 92.4 | 94.4/5.6 | 37.2 |
| 6602 | 2.70 | 1.00 | 0.11 (4,6) | 1.24 | 485 | 1.22 | 0.07 | 1784 | 1.15 | 1.38 | 89.9 | 93.9/6.1 | 43.6 |

(1) Soluble inorganic chloride determined by Mohr method.
(2) Based on the amount of MgCl$_2$ converted to Me$_2$Mg.
(3) Employed old lab sample anhydrous MgCl$_2$ - possible source Western Zirconia, Inc.
(4) Employed anhydrous MgCl$_2$ from Rossborough, Cleveland, Ohio.
(5) MgCl$_2$ used "as is" - not dried - H$_2$O content = 0.7 wt. %.
(6) Prior to use, MgCl$_2$ dried in oven (240° C.) for two hours.

TABLE II

INCREASING MAGNESIUM CONTENT OF A MeLi/Me$_2$Mg (9406) SOLUTION EMPLOYING VARIOUS SOURCES OF ANHYDROIUS MAGNESIUM CHLORIDE

| Experiment Number | MeLi 9406 (1) MeM Millimoles | MgCl$_2$ Millimoles | Total Base N. | Chloride (2) Titration ppm | NMR MeM M. | NMR THF/MeM Mole Ratio | Magnesium Titration M. | Utilization MgCl$_2$ % | New Composition MeLi/Me$_2$Mg Mole Ratio |
|---|---|---|---|---|---|---|---|---|---|
| 6605 | 65 | 8.1 (4,7) | 1.24 | 1084 | 1.21 | 1.31 | 0.17 | 59.9 | 84.1/15.9 |
| 6613 | 65 | 9.0 (4,6) | 1.24 | 1240 | 1.22 | 1.27 | 0.27 | 88.5 | 72.2/27.8 |
| 6606 | 65 | 10.2 (5,7) | 1.25 | 785 | 1.21 | 1.38 | 0.23 | 77.5 | 77.5/22.5 |
| 6612 | 65 | 11.7 (5,6) | 1.26 | 570 | 1.26 | 1.31 | 0.29 | 92.7 | 70.1/29.9 |
| 6614 | 65 | 54.6 (4,6) | 1.20 | 810 (9) | 1.22 | 1.12 | 0.69 | N.A. (8) | 0/100 |

(1) Employed 50 ml MeLi-9406 solution (Exp. No. 6595) - Total Base = 1.30N, Mg titration = 0.073M, THF/MeM = 1.21 mole ratio, composition MeLi/Me$_2$Mg = 94/06 mole ratio.
(2) Soluble inorganic chloride determined by Mohr method.
(3) Based on the amount of MgCl$_2$ converted to Me$_2$Mg.
(4) Employed anhydrous MgCl$_2$ from Rossborough, Cleveland, Ohio.
(5) Employed old lab sample anhydrous MgCl$_2$ - possible source Western Zirconia, Inc.
(6) MgCl$_2$ used "as is" - not dried - H$_2$O content 0.7 wt. %.
(7) Prior to use, MgCl$_2$ dried in an oven (240° C.) for two to three hours.
(8) Not applicable because excess MgCl$_2$ was employed.
(9) Sample filtered through a 1 micron filter prior to analysis.

We claim:

1. A process for producing organometallic and organobimetallic compositions comprising reacting two moles of an alkali metal with one mole of an organo halide and 0.02 to 0.5 moles of an anhydrous magnesium halide selected from magnesium bromide, magnesium chloride, magnesium iodide and mixtures there of, in a liquid hydrocarbon solvent containing a limited amount of a Lewis base to produce a product containing 0 to 98 mole percent of an alkali metal alkyl compound and 2 to 100 mole percent of a dialkylmagnesium compound.

2. The process of claim 1 wherein the organic halide has the formula RX in which R is selected from alkyl, cycloalkyl, α-alkylene, alkenyl and aryl groups and X is selected from bromide, chloride and iodide.

3. The process of claim 1 wherein the Lewis base is selected from tetrahydrofuran and methyltetrahydrofuran.

4. The process of claim 1 wherein the hydrocarbon solvent is selected from the group consisting of C$_5$ to C$_{10}$ aliphatics, C$_6$ to C$_{10}$ cycloaliphatics and aromatics selected from benzene, toluene, ethylbenzene and cumene.

5. A process according to claims 1 or 2 in which the liquid hydrocarbon solvent is selected from the group consisting of C$_5$ to C$_{10}$ aliphatics, C$_6$ to C$_{10}$ cycloaliphatics and aromatic hydrocarbons selected from the group consisting of benzene, toluene, ethylbenzene and cumene.

6. The process according to claims 1 or 2 in which the alkali metal is selected from lithium, potassium and sodium.

7. A process according to claims 1 or 2 in which the organic halide is selected from the group consisting of methyl chloride and ethyl chloride.

8. A process according to claims 1 or 2 in which the ratio of Lewis base to organic halide is between 0.05 and 2.0 moles of Lewis base per mole of organo halide.

9. A process according to claims 1 or 2 in which organic halide is represented by the formula RX in which X is a radical selected from the group consisting of chloride, bromide and iodide radicals and R is a radical selected from the group consisting of methyl, ethyl, n-butyl, sec-butyl, 2-ethylhexyl, n-octyl, cyclohexyl, 1,4-butylene, phenyl, cumyl, benzyl, tolyl, vinyl and crotyl radicals and mixtures thereof.

10. A process according to claims 1 or 2 in which the reaction is conducted at a temperature between 0° C. and 50° C.

11. A process according to claims 1 or 2 in which the reaction is conducted at a temperature between 25° C. and 35° C.

12. A process according to claim 1 in which the organic halide is methyl chloride, the alkali metal is lithium, the solvent is cumene and the Lewis base is tetrahydrofuran.

13. A process according to claim 12 in which there is 0.05 to 2.0 moles of tetrahydrofuran per mole of methyl chloride.

14. A process according to claim 12 in which there is 1.2 to 1.5 moles of tetrahydrofuran per mole of methyl chloride.

* * * * *